United States Patent
Wildon

[19]

[11] Patent Number: 6,163,728
[45] Date of Patent: Dec. 19, 2000

[54] EPICARDIAC PACING LEAD

[76] Inventor: Michael Peter Wildon, 10 Princes Street, Cootesloe, Western Australia, Australia

[21] Appl. No.: 09/202,275

[22] PCT Filed: Jun. 11, 1997

[86] PCT No.: PCT/AU97/00368

§ 371 Date: Dec. 11, 1998

§ 102(e) Date: Dec. 11, 1998

[87] PCT Pub. No.: WO97/47351

PCT Pub. Date: Dec. 18, 1997

[30] Foreign Application Priority Data

Jun. 11, 1996 [AU] Australia ................................ P00374

[51] Int. Cl.[7] ...................................................... A61N 1/05
[52] U.S. Cl. ............................................ 607/132; 607/126
[58] Field of Search ........................... 607/116, 119, 607/122, 129–132; 600/372–375

[56] References Cited

U.S. PATENT DOCUMENTS

| | | | |
|---|---|---|---|
| 3,598,128 | 8/1971 | Chardack | 607/9 |
| 4,010,758 | 3/1977 | Rockland et al. | 607/131 |
| 4,146,037 | 3/1979 | Flynn et al. | |
| 4,306,560 | 12/1981 | Harris | |
| 4,369,880 | 1/1983 | Giggey et al. | |
| 5,427,243 | 6/1995 | Roshdy | |
| 5,503,266 | 4/1996 | Kalbfeld et al. | |

FOREIGN PATENT DOCUMENTS

| | | |
|---|---|---|
| 13475/95 | 12/1995 | Australia . |
| 30104/95 | 2/1996 | Australia . |
| 0 715 865 A2 | 6/1996 | European Pat. Off. . |
| 0773 036 A1 | 5/1997 | European Pat. Off. . |
| WO 94/27666 | 12/1994 | WIPO . |

*Primary Examiner*—George R. Evanisko
*Attorney, Agent, or Firm*—Holland & Hart LLP

[57] ABSTRACT

The present invention provides an a storage device for an epicardiac pacing lead having a flexible cable. In particular, the storage device of the present invention accommodates the flexible cable in the stored condition and provides a spool and freely rotatable spindle that allows the stored cable to be unwound as it is progressively withdrawn from the storage device.

18 Claims, 10 Drawing Sheets

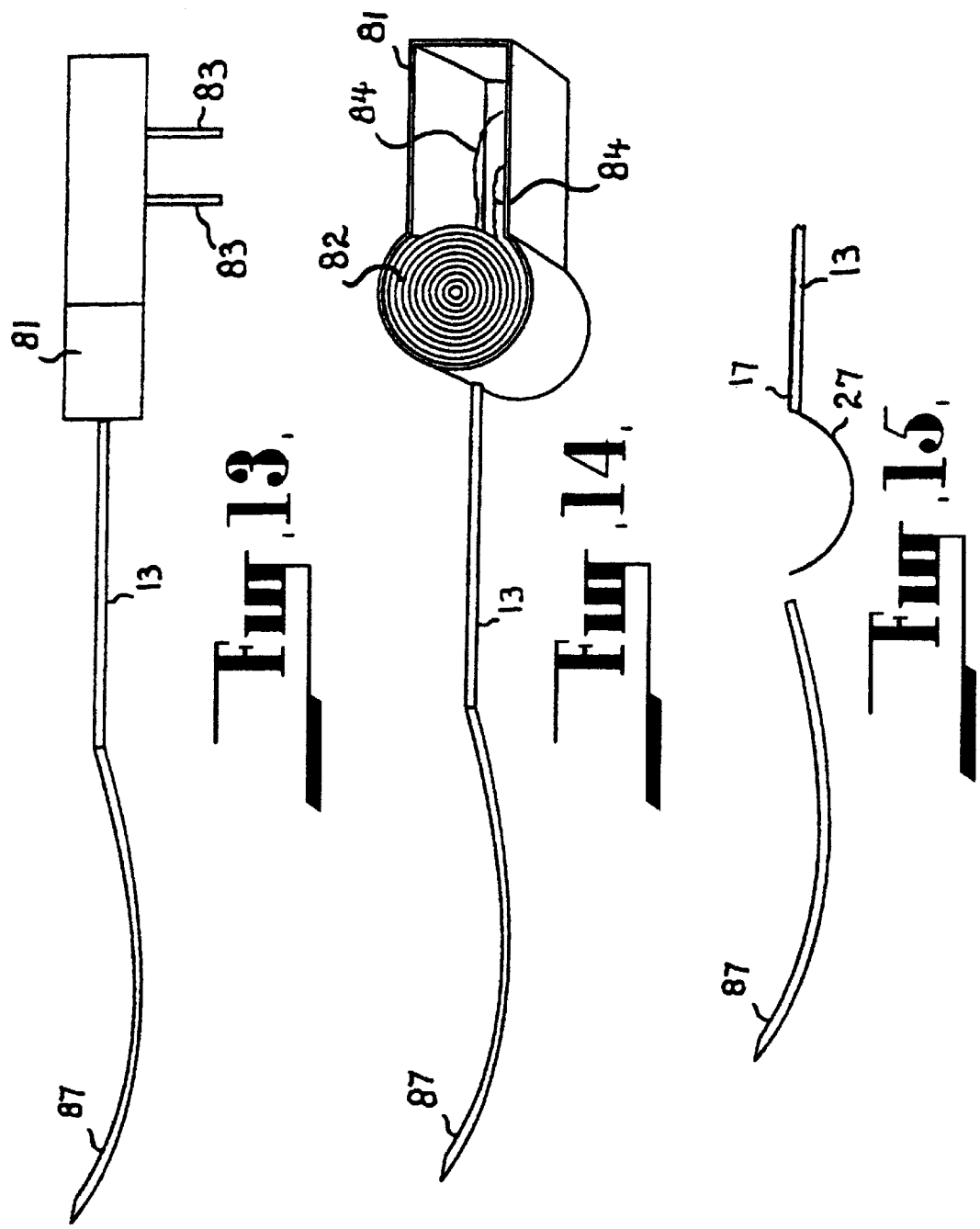

EPICARDIAC PACING LEAD

TECHNICAL FIELD

This invention relates to an epicardiac pacing lead.

BACKGROUND OF THE INVENTION

An epicardiac pacing lead is used to apply electrical stimulation to the heart of a cardiac surgical patient from an external pacemaker. Electrical stimulation is normally used after surgical procedures on cardiac patients to correct arrhythmic beating of the heart. The electrical stimulation may be applied to the atrium, to the ventricle or sequentially to the atrium and the ventricle of the heart.

The pacing lead has a stimulating electrode at one end, the other end is adapted for electrical connection to the pacemaker. The pacing electrode is implanted in the body of the patient, with the stimulating electrode in electrical contact with the heart. The conventional pacing lead is affixed to the external surface of the heart with a suture and is threaded with a thoracic needle (at its other end) through the chest or upper abdominal wall of the patient for connection to the external pacemaker via an external extension lead commonly known as a patient cable.

Typically, such a pacing lead is supplied for use in a stored condition in which it is usually wrapped on a card and sometimes wound into a coil. Prior to implantation into the body of a patient, the pacing lead is manually unwrapped from the card and unwound from the coil so that it can be installed by threading through the body of the patient.

SUMMARY OF THE INVENTION

The present invention seeks to provide a pacing lead which can be progressively withdrawn from a storage condition during the installation procedure.

Accordingly, the present invention provides an epicardiac pacing lead comprising a flexible cable and a storage means accommodating the cable in a stored condition, whereby the cable can be progressively withdrawn from the storage means during installation of the cable in the body of a patient.

In one arrangement the storage means may comprise a spool.

Preferably, the spool is supported in a manner which allows it to rotate for unwinding of the cable therefrom. For this purpose, the spool may be rotatably supported on a central spindle which can be gripped. Conveniently, the spindle is adapted to be gripped between the ends thereof. With this arrangement, the spool may be supported in the hand of a user, with the spindle being gripped at its ends between the thumb and a finger.

In another arrangement, the storage means may comprise a structure supporting the cable stored in a folded condition. Conveniently, the cable is folded back and forth about itself so that it can progressively unfold as it is withdrawn from the structure. One structure may comprise a casing having a pair of spaced apart surfaces defining a gap therebetween in which the folded cable is frictionally retained between said surfaces.

The cable may have a distal end, a proximal end, an electrode means associated with the distal end and a connector means associated with the proximal end for connection to an external pacemaker. Typically, the distal end of the cable is fitted with a heart needle for threading the cable into contact with the heart.

In one arrangement, the proximal end of the cable may receive means for threading the cable through portion of the body of the patient. Such means may comprise a thoracic needle fitted onto the proximal end of the cable, over the connector means. The thoracic needle is intended to be removed from the cable to expose the connector means after the cable has been threaded through the body of the patient. In this arrangement, the pacing lead is preferably supplied with the thoracic needle fitted onto the proximal end of the cable.

In another arrangement, the distal end of the cable may receive means for threading the cable through portion of the body of the patient. Such means may comprise a thoracic needle fitted onto the distal end of the cable, typically over the heart needle. The thoracic needle is removed from the cable to expose the heart needle after the cable has been threaded through the body of the patient. In this arrangement, the pacing lead is preferably supplied with the thoracic needle fitted onto the distal end of the cable.

The storage means may have attachment means to which the proximal end of the cable can be releasably attached to prevent unintentional withdrawal of the cable from the storage means. The attachment means may comprise a body of resilient material such as sponge into which the outer (pointed) end of the thoracic needle can be embedded when it is fitted onto the proximal end of the cable thereby to secure the proximal end to the storage means. The body of resilient material may be mounted onto one side of the storage means.

The distal end of the cable may also be releasably attached to the storage means. In this regard, the outer (pointed) end of the heart needle can also be embedded into the body of resilient material to secure the distal end of the cable to the storage means. Alternatively, a separate body of resilient material may be provided for such a purpose.

Because the cable has a stored condition from which it can be progressively withdrawn, it can be made to a length which is sufficient for it to be connected directly to the external pacemaker, so avoiding the need for an extension lead (patient cable) which is used to connect a conventional pacing lead to an external pacemaker. Without the storage means, a pacing lead of such length would be difficult to manage during the surgical procedure. The ability to use the pacing lead without a conventional extension lead is beneficial in that it avoids various problems encountered with such extension leads including: (a) the difficulty in obtaining good electrical connections; (b) the limited life span owing to degradation when subjected to heat for sterilisation; and (c) the general inconvenience and cost involved in having extension leads not only available for use but also in a sterile condition.

The pacing lead according to the invention may be monopolar, bipolar, quadpolar or indeed any other appropriate configuration.

Where the pacing lead is bipolar, the cable comprises two electrical conductors (such as wires) insulated with respect to each other, and two of said electrodes one associated with each wire. The two electrodes define an anode and a cathode.

The connector means may comprise a connector pin on each wire at the proximal end of the pacing lead.

In the bipolar arrangement, the two electrodes may be spaced along the cable. It is desirable for the electrodes to be positioned as closely together as is possible while maintaining sufficient separation to prevent electrical shorting therebetween. With the present arrangement, a spacing of about 3 mm between the electrodes can be achieved.

This spacing is in contrast to the standard protocol for cardiac pacing which stipulates a spacing of 10 mm between electrodes. It has, however, been found that closely positioning the electrodes down to a gap of about 3 mm allows significantly lower pacing thresholds to be achieved and provides for better electro-physiological sensing.

The close spacing between the electrodes allows the pacing lead to be implanted so as to apply electrical stimulation to the atrium or to the ventricle.

Furthermore, because of the close spacing of the electrodes, as well as the design of the electrodes and the heart needle, only one pass of the heart needle through the myocardium is required to implant both electrodes within the desired portion of the myocardial tissue.

The electrode which is closer to the distal end of the cable is smaller than the other electrode.

The larger electrode may comprise a contact surrounding both of the wires and is electrically connected to one of the two wires.

The smaller electrode may comprise a contact on or defined by a portion of the other of the two wires. Conveniently, the smaller electrode comprises an exposed section of the other wire.

The exposed section of said other wire may be formed by stripping the insulation surrounding that section, the stripped insulation comprising a plurality of strips each of which is attached at a common end thereof to the remainder of the insulation. With this arrangement, the plurality of strips are movable between a collapsed condition in which the strips lie snugly against the exposed section of the wire and an extended condition in which the strips project outwardly of the wire to provide a barbed formation. The flexible nature of the insulation has the effect of biasing the strips into the extended condition.

The barbed formation is oriented to allow the distal end to be easily threaded through the myocardial tissue and to resist movement in the reverse direction. The barb formation can, however, flex back upon itself because of the flexible nature of the insulation to allow the pacing lead to be withdrawn from the body of the patient in the conventional manner by pulling thereof in the reverse direction.

The heart needle is detached from the pacing lead once the latter has been implanted in the body of the patient. This can be done simply by cutting the heart needle off from the distal end of the cable. Removal of the heart needle from the cable is necessary so that the pacing lead can be withdrawn from the body of the patient after completion of the pacing treatment.

Conventional heart needles, which typically have working ends which are either entirely straight or entirely curved, can be used with the pacing lead. It may, however, be advantageous to use a heart needle which has a working end comprising two sections being a leading section which is straight followed by a following section which is curved. The leading section allows the needle to obtain sufficient depth of penetration into the tissue into which the distal end of the cable is being threaded and the curved section allows the needle to turn to move out of the tissue.

BRIEF DESCRIPTION OF THE DRAWINGS

The invention will be better understood by reference to the following description of several specific embodiments thereof as shown in the accompanying drawings in which:

FIG. 13 is a schematic side view of an epicardiac pacing lead according to a third embodiment;

FIG. 14 is a schematic perspective view of the lead shown in FIG. 13 with part of a housing removed to reveal the cable in a stored condition; and FIG. 15 is a fragmentary view of the distal end of the cable showing a thoracic needle removed to expose a heart needle on the end of the cable.

DESCRIPTION OF PREFERRED EMBODIMENTS

Figure 1:
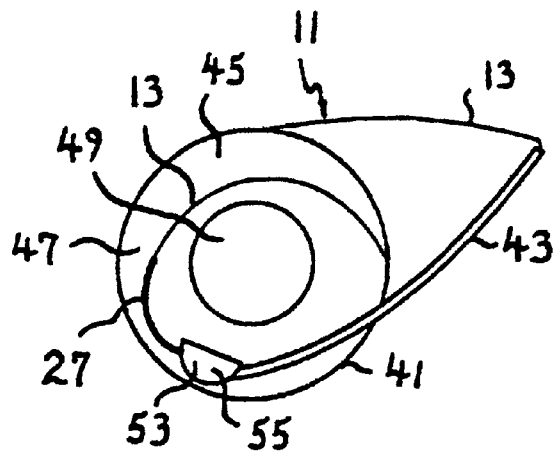
FIG. 1 is a schematic side view of an epicardiac pacing lead according to the embodiment, the pacing lead being shown in a stored condition with the cable thereof wound onto the spool.

The embodiments shown in the drawings are each directed to a temporary bipolar myocardial pacing lead 11 which can provide electrical stimulation to either the atrium or the ventricle of a cardiac surgical patient.

Referring now to FIGS. 1 to 10, there is shown a pacing lead 11 according to the first embodiment comprising a flexible cable 13 having a proximal end 15 and a distal end 17. The cable 13 is composed of a first insulated conductor wire 21 and a second insulated conductor wire 22. The insulation materials on the first and second conductor wires 21, 22 are fused together to form a unitary structure for the cable 13.

The cable 13 is provided with a connector means 23 at the proximal end 15 thereof for connection to an external pacemaker (not shown) of known kind. The connector means 23 comprises a connector pin 25 fitted onto each of the first and second conductor wires 21, 22.

A heart needle 27 is fitted onto the distal end 17 of the cable 13, as will be explained in more detail later.

Electrode means 30 are associated with the cable at the distal end thereof. The electrode means 30 comprises a first electrode 31 electrically connected to the first wire 21 and a second electrode 32 electrically connected to the second wire 22.

The two electrodes 31, 32 are axially spaced along the cable 13, with the distance between the electrodes being small (typically about 3 mm).

The first electrode 31 comprises a contact 33 which surrounds both of the wires 21, 22 but which is only connected electrically to the first wire 21. The contact 33 tapers inwardly at the ends thereof in somewhat of a rounded fashion to assist movement through heart tissue during implantation and removal of the pacing cable.

The first conductor wire 21 terminates at the contact 33. The second conductor wire 22 extends beyond the contact 33 and terminates at the heart needle 27.

The second electrode 32 is provided on the portion of the second conductor wire 22 extending beyond the contact 33 such that it is closer to the distal end of the cable 13 than the first electrode 31.

Figure 4:
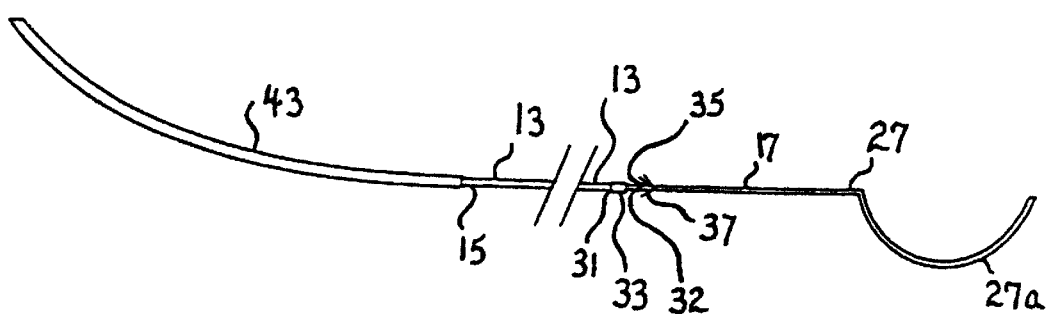
FIG. 4 is a schematic fragmentary view of the cable showing the proximal and distal ends thereof, with a thoracic needle attached to the proximal end.
Figure 5:
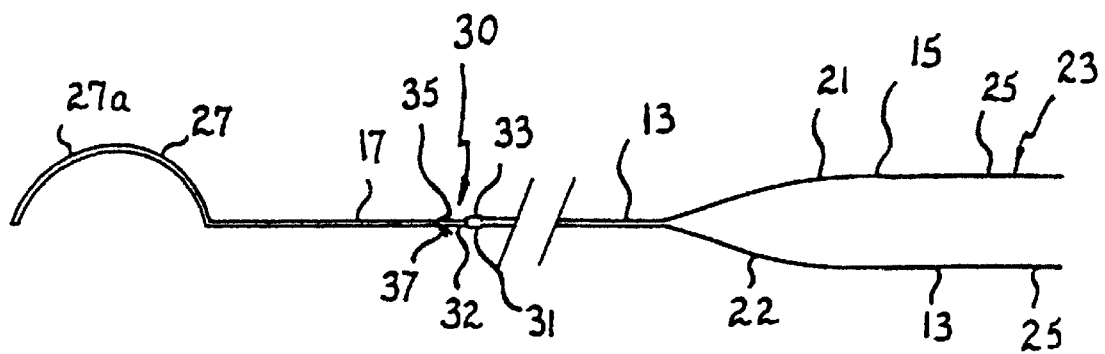
FIG. 5 is a view similar to FIG. 4 except that the thoracic needle has been removed from the proximal end to expose the connector means.
Figure 6:
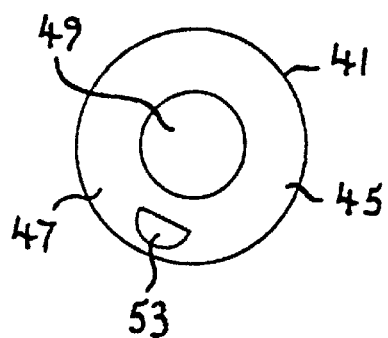
FIG. 6 is a schematic side view of the spool.
Figure 7:
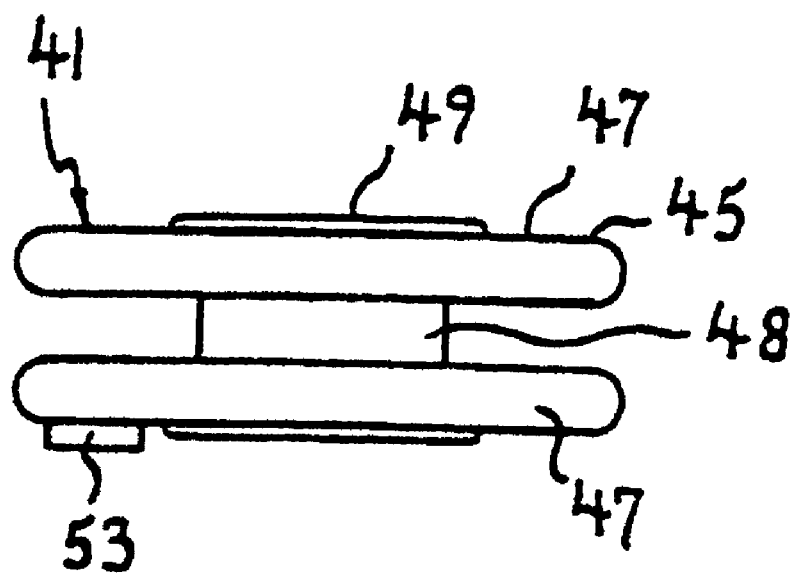
FIG. 7 is a schematic end view of the spool.

The second electrode 32 comprises an exposed section 35 of the second wire 22. The exposed section 35 is formed by stripping the insulation material surrounding that section. The stripped insulation comprises a plurality of strips 37 each of which remains attached at a common end thereof to the remainder of the insulation about the wire 22. The strips 37 are movable between a collapsed condition in which they occupy their original position snugly against the exposed section 35 of the wire, and an extended condition (as shown in FIGS. 4 and 5) in which the strips 37 project outwardly of the wire to provide a barbed formation. The flexible nature of the insulation has the effect of biasing the strips 37 into the extended condition.

Figure 8:
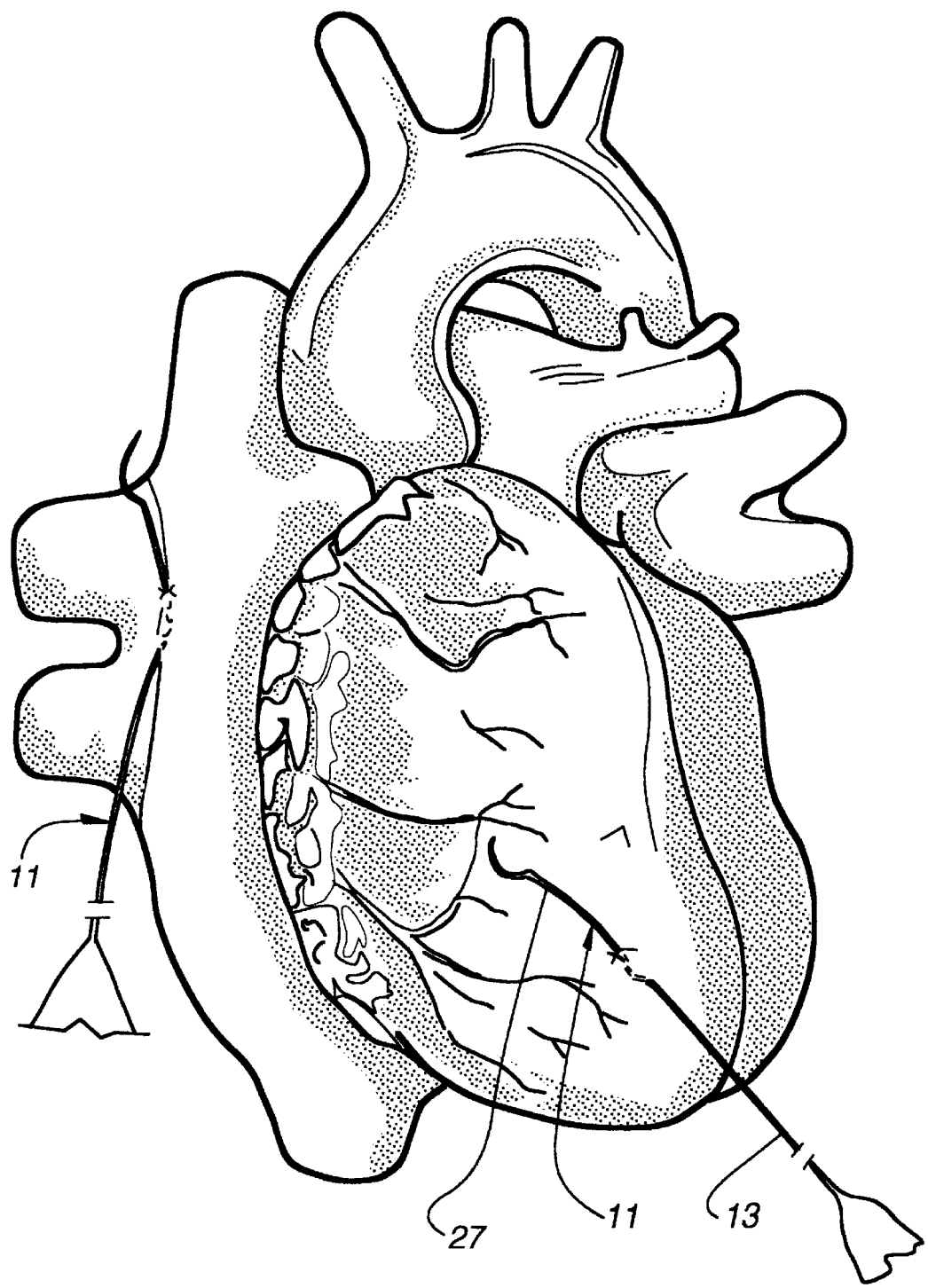
FIG. 8 is a schematic view showing for the purpose of illustration only two of the pacing leads implanted into the body of a patient, one positioned to provide electrical stimulation to the atrium and the other positioned to provide electrical stimulation to the ventricle.
Figure 9:
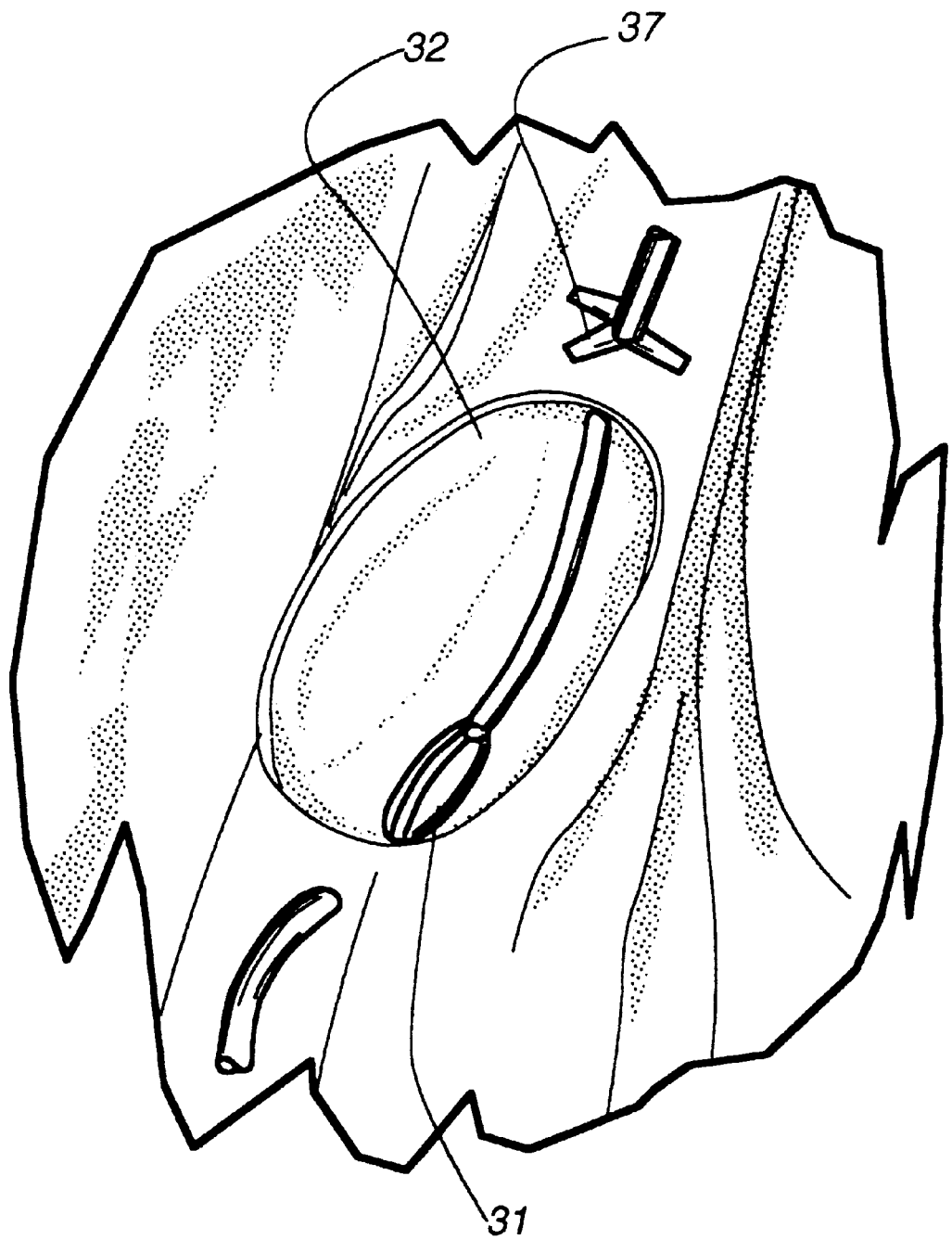
FIG. 9 is a detailed view of part of FIG. 8 showing the electrode of the particular pacing lead in contact with the atrium.
Figure 10:
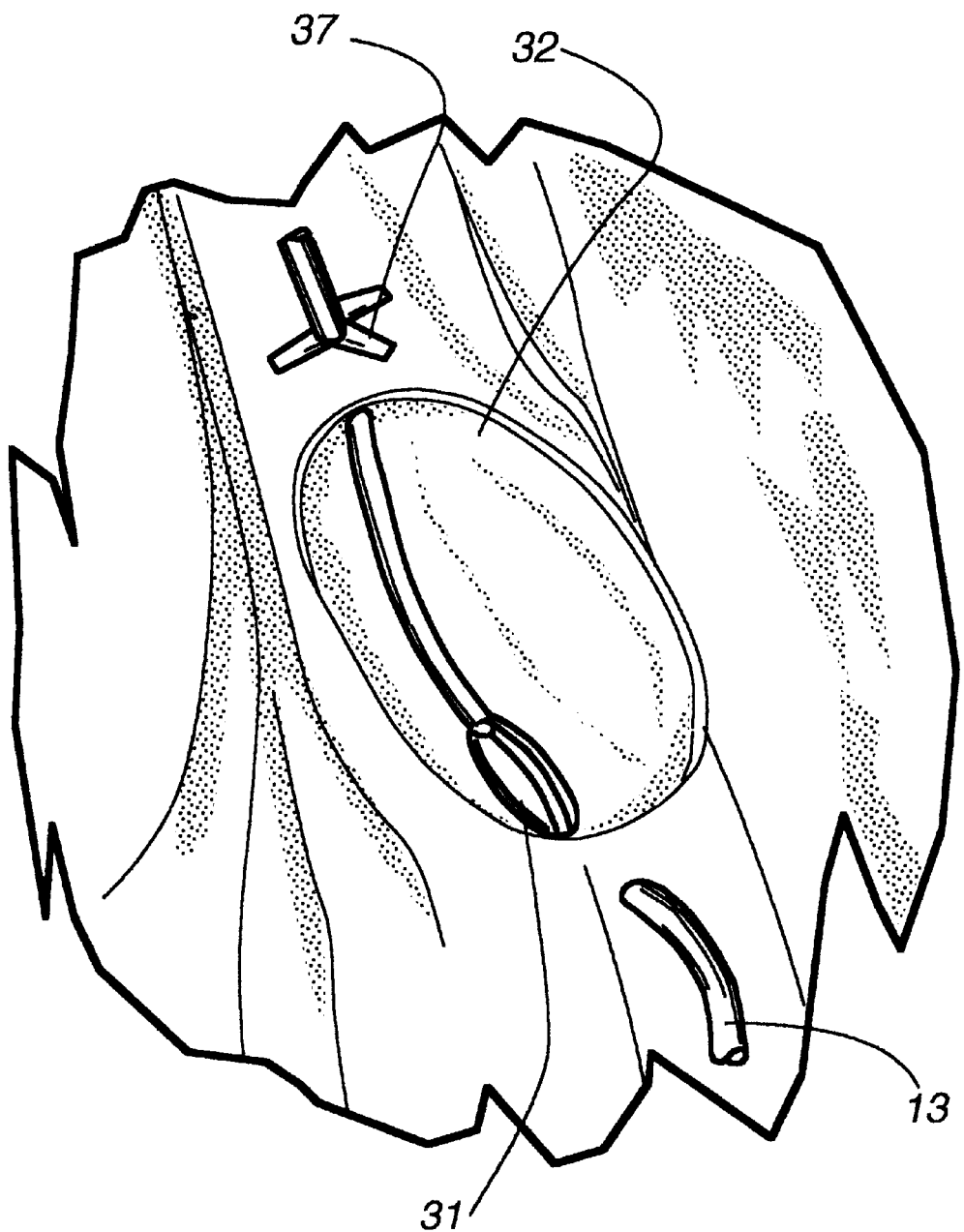
FIG. 10 is a detailed view of a further part of FIG. 8 showing the electrodes of the particular pacing lead in contact with the ventricle.

The barbed formation provided by the strips 37 is arranged to deflect into the inward position during threading of the cable 13 into heart tissue to position the electrodes 31, 32 in the myocardium and then to return to the extended condition (as shown in FIGS. 8, 9 and 10) upon exiting from the tissue thereby to gently oppose reverse movement of the cable. In this way, the barbed formation assists in holding the electrodes 31, 32 in a stable position in the myocardium.

Because of the close positioning of the electrodes 31, 32, they can be positioned within the atrial or ventricular myocardium with one single pass of the heart needle 27. Once the electrodes are positioned in the myocardial tissue, the heart needle 27 is cut off the cable 13 and removed.

The heart needle 27 in this embodiment has a working end 27a which is curved. It has been found that better penetration into the myocardial tissue can be achieved with a heart needle having a working end which comprises a leading section which is straight and a following section which is curved. The trailing end of the heart needle, which is rearward of the working end, is preferably straight. It is the trailing end to which the cable 13 is attached.

The cable 13 is of sufficient length to allow it to be connected directly to the external pacemaker by means of the connector pins 25 without requiring a conventional extension lead.

Because of the length of the cable 13, it is stored in a sterile condition on a storage means which in this embodiment comprises a spool 41 about which it is wound in readiness for use.

In this condition, the cable 13 has a conventional thoracic needle 43 fitted onto its proximal end over the connector means 23. The thoracic needle 43 is used to thread the cable 13 through the abdominal wall of the patient in known manner. The thoracic needle 43 is subsequently removed from the cable to expose the connector means 23 for connection to the external pacemaker.

Figure 2:
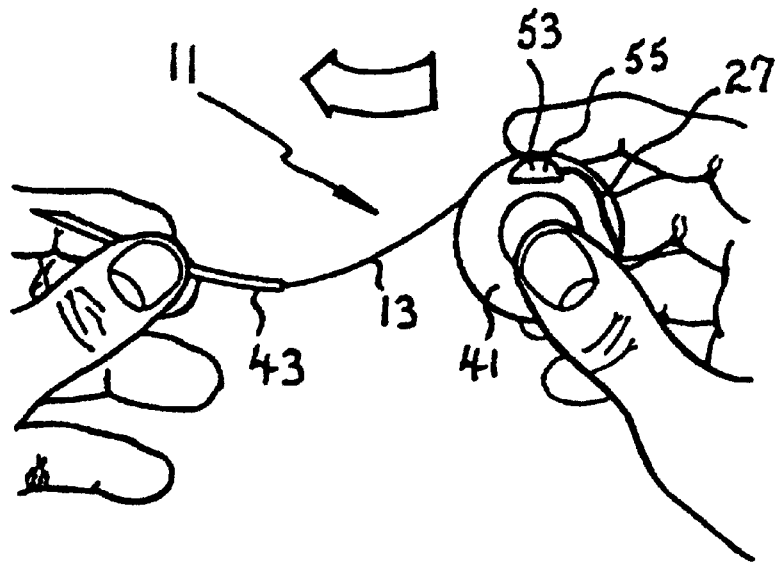
FIG. 2 is a schematic view of the pacing lead with the cable commencing to be unwound from the spool.
Figure 3:
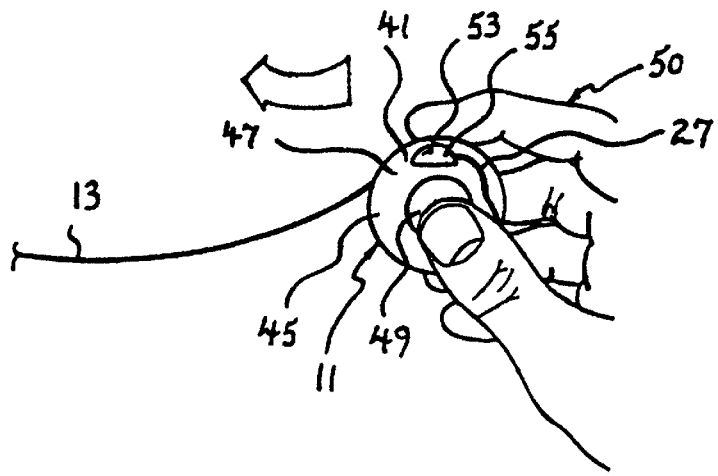
FIG. 3 is a view similar to FIG. 2 showing the cable continuing to be unwound from the spool.

The spool 41 about which the cable 13 is wound comprises a reel 45 having opposed sides 47 and a central hub 48 positioned between the sides. The reel 45 is freely rotatable on a central spindle 49 which passes through the hub and extends beyond the sides 47. With this arrangement, the spool 41 can be held in the hand 50 of a surgeon installing the pacing lead 11, with the spindle 49 being gripped between the thumb and a finger so as to allow the reel 45 to rotate as the cable 13 is pulled to unwind it from the spool, as shown in FIGS. 2 and 3. The rate at which the cable 13 unwinds from the spool 41 can be controlled by pressing a further finger against the reel as it rotates.

The cable 13 is wound onto the spool in a manner such that the proximal end fitted with the thoracic needle 43 unwinds first.

During the surgical procedure to install the pacing lead 11, the surgeon holds the thoracic needle 43 in one hand and the spool 41 in the other hand, as shown in FIG. 2. The cable 13 is progressively unwound from the spool 41 as it is threaded through the abdominal wall of the patient. This regulated delivery of the cable ensures that the cable does not become unwieldy and also assists in maintaining sterile conditions.

The spool can be discard once the cable 13 has been completely unwound from it.

Once the cable 13 has been removed from the spool 41, the heart needle 27 is accessible and can be used to thread the distal end of the cable into the myocardial tissue to position the two electrodes 31, 32 in electrical contact with the heart, as described previously.

The spool 41 is provided with an attachment means 53 by which both the heart needle 27 and the thoracic needle 43 can be releasably fixed in position to prevent unintentional unwinding of the cable 13 from the spool. Such attachment means 53 comprises a body 55 of resiliently flexible material such as sponge rubber bonded onto the exterior of one of the sides 47 of the reel. The outer (pointed) ends of the heart needle 27 and the thoracic needle 43 can each be pushed into the body 55 to releasably secure needles in position. The body 55 also shields the pointed ends of the needles 27, 43 when the pacing lead 11 is in the stored condition. Each needle is then withdrawn from the body 55 as required.

This arrangement provides a simple yet highly effective way of preventing unintentional unwinding of the cable 13 from the spool 41. It will, of course, be appreciated that a separate attachment means may be provided for each needle 27, 43. Further, it will be appreciated that the or each attachment means may take any other suitable form such as a notch in the spool to releasably grip each needle.

Figure 11:
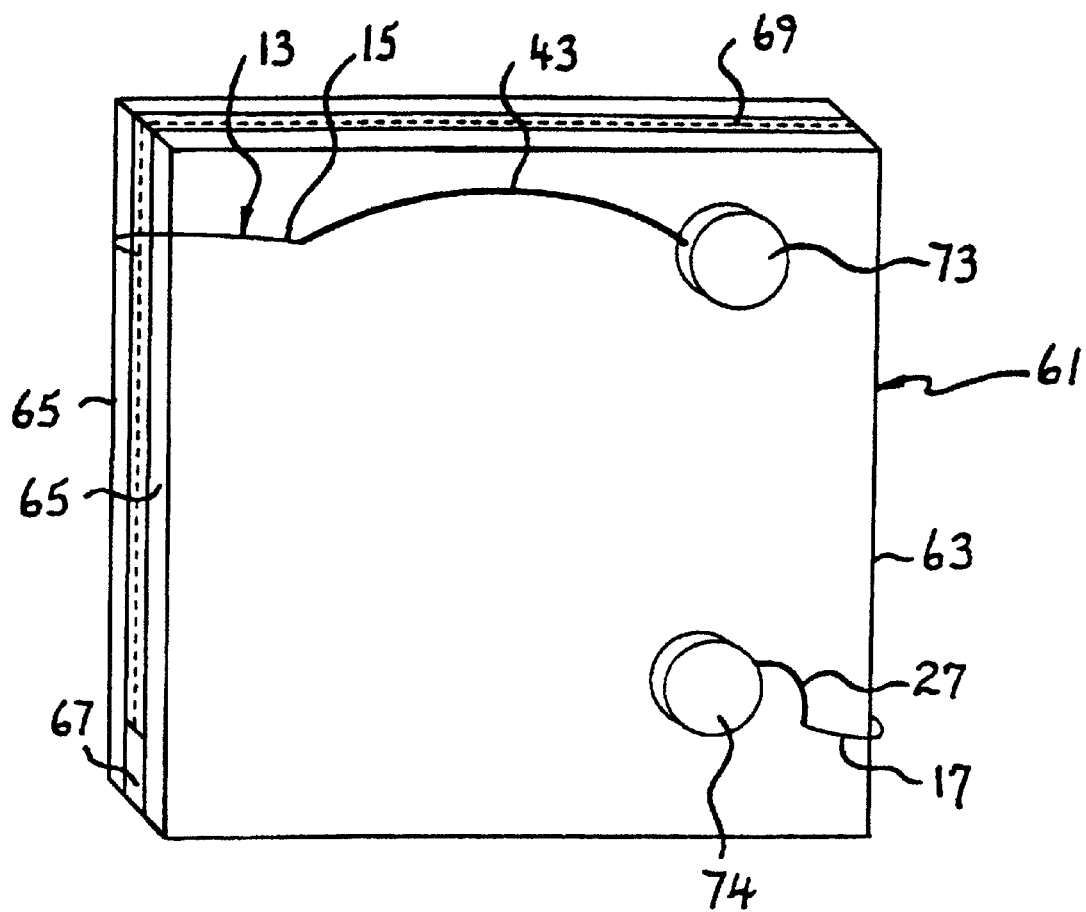
FIG. 11 is a schematic perspective view of an epicardiac pacing lead according to a second embodiment.
Figure 12:
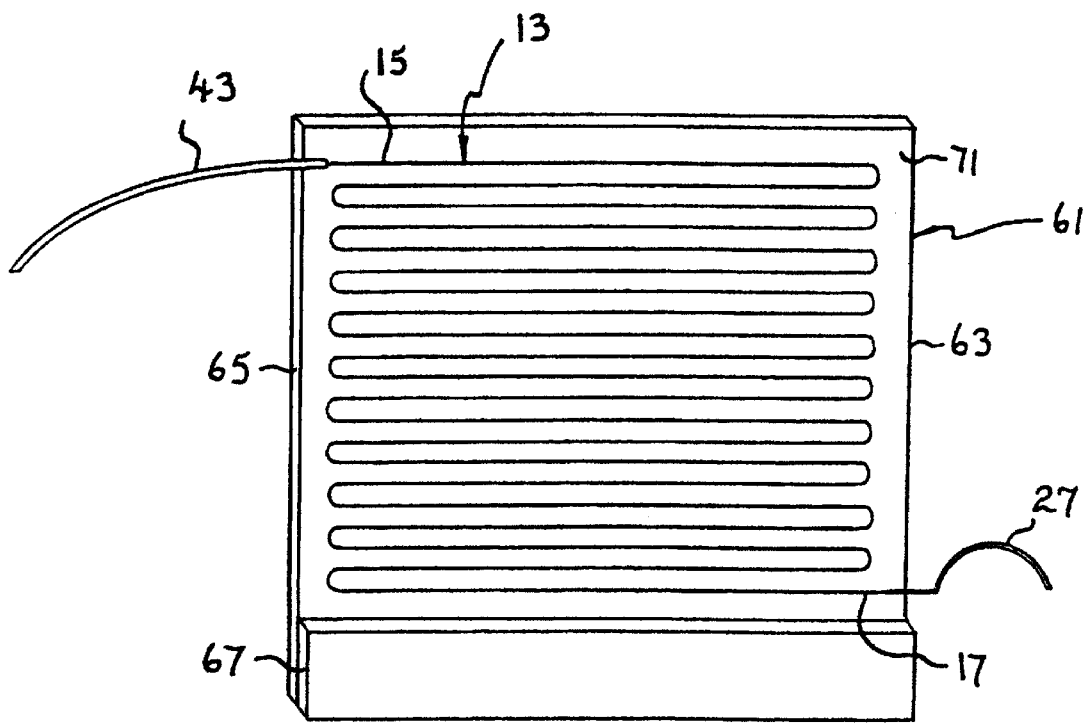
FIG. 12 is a view similar to FIG. 11 except that part of a casing accommodating the cable has been removed to show the cable stored in a folded condition.

Referring now to FIGS. 11 and 12 of the drawings, the epicardiac pacing lead according to a second embodiment comprises a flexible cable 13 accommodated in a stored condition in a storage means 61. The flexible cable 13 is of a similar construction to the cable described in relation to the first embodiment and has a heart needle 27 fitted onto the distal end 17 and a thoracic needle 43 fitted onto the proximal end 15 over connector means (not shown).

The storage means 61 comprises a casing 63 having a pair of spaced apart walls 65. The spaced apart walls 65 are fixed with respect to each other by a spacer 67 between the walls adjacent one end thereof. A gap 69 is defined between the spaced apart walls 65, the gap being bounded by inner faces 71 of the two walls. The gap 69 opens onto the periphery of the casing apart from at the location occupied by the spacer 67.

The cable 13 is accommodated in a folded condition in the gap 69 within the casing 63. As best seen in FIG. 12 of the drawings, the cable 13 is folded back and forth about itself to assume a collapsed condition within the casing. With this arrangement, the cable can be progressively withdrawn from the folded condition from either the distal end or the proximal end thereof.

The cable 13 is retained in the folded condition within the gap 69 of the casing 63 by virtue of frictional contact between the cable and the inner faces 71 of the side walls 65. Cushioning material (not shown) such as a layer of flexible foam may be provided on the inner face 71 of one or both of the side walls 65 to assist in maintaining the cable in the folded condition within the gap and facilitate its ready withdrawal upon pulling of either the distal end or the proximal end of the cable.

Means are provided for releasably securing the heart needle 27 and the thoracic needle 43 to the casing so as to prevent unintentional withdrawal of the cable and to shield the pointed ends of those needles. Such means comprise a first body of flexibly resilient material 73 (such as sponge rubber) bonded onto the exterior of the casing 63 and into which the thoracic needle 43 may be embedded, and a second body 74 of similar material bonded onto the exterior of the casing into which the heart needle 27 may be embedded.

The pacing lead according to this embodiment can be used in a similar fashion to the pacing lead of the first embodiment in that the cable can be progressively withdrawn from the storage means as it is threaded through the body of a patient.

The storage means 61 of this embodiment has an advantage over the storage means provided by the spool 41 of the first embodiment in that the cable can be removed with either the distal end or the proximal end leading.

While in the embodiment the thoracic needle is shown fitted onto the proximal end, it could be fitted onto the distal end so as to cover the heart needle to thereby allow the cable to be threaded through the body of the patient in an inward direction from the exterior.

Referring now to FIGS. 13, 14 and 15, the pacing lead according to the third embodiment comprises a flexible cable 13 having a proximal end (not shown) and a distal end 17. The flexible cable 13 is accommodated in a stored condition in a housing 81 incorporating a reel 82 about which the cable is wound in the stored condition. The housing 81 incorporates a pair of electrical pins 83 to which the two conductor wires of the cable 13 are connected by wires 84. The pins 83 are adapted to be plugged directly into conventional sockets of an external pacemaker. The sockets of the external pace maker would normally receive the ends of an extension lead (patient cable) but in this case the pins 83 are plugged directly into them.

The distal end 17 of the flexible cable 13 is fitted with a heart needle 27.

In this embodiment, the flexible cable 13 is withdrawn from the storage means defined by the reel 82 within the housing 81 with the distal end 17 leading. The distal end 17 of the cable 13 therefore needs to be threaded through the abdominal wall of the patient and for this purpose a thoracic needle 87 is fitted onto the distal end over the heart needle 27. The heart needle 27 is of a flexible construction so that it can deform into a condition which will allow fitting of the thoracic needle 87 onto it. The thoracic needle 87 is used to thread the cable 13 through the abdominal wall of the patient in known manner and then is subsequently removed from the cable 13 to expose the heart needle 27 for use in its normal manner.

With this embodiment, only the amount of cable 13 necessary for the particular surgical procedure is required to be unwound from the reel 82 and any excess can simply be returned to the reel.

From the foregoing, it is evident that the present embodiments each provide a simple yet highly effective arrangement for providing a pacing lead which can be of sufficient length to avoid the need for an extension lead without being unwieldy in use.

It should be appreciated that the scope of the invention is not limited to the scope of the embodiments described.

What is claimed is:

1. An apparatus comprising:
   a storage device; and
   an epicardiac pacing lead having a flexible cable,
   the storage device accommodates the flexible cable in a stored condition, the storage device includes a spool and a spindle, the spool is freely rotatable on the spindle such that the flexible cable can be unwound while the flexible cable is progressively withdrawn from the storage device during installation of the flexible cable in a patient.

2. The apparatus according to claim 1 wherein the flexible cable has a distal end, a proximal end, and at least one electrode coupled to the distal end and a connector means coupled to the proximal end for connecting the proximal end of the flexible cable to an external pacemaker.

3. The apparatus according to claim 2 wherein the distal end of the flexible cable is fitted with a heart needle for threading the flexible cable into contact with a heart.

4. The apparatus according to claim 1 wherein the flexible cable has a proximal end, said proximal end having a means for threading the flexible cable through a portion of the patient.

5. The apparatus according to claim 4 wherein the flexible cable has a connecting means coupled to the proximal end for connecting the proximal end of the flexible cable to an external pacemaker and where the threading means comprises a needle removably fitted onto the proximal end of the cable over the connector means.

6. The apparatus according to claim 1 wherein the storage device has an attachment means for releasably attaching a distal end of the flexible cable to the storage device to prevent unintentional withdrawal of the flexible cable from the storage device.

7. The apparatus according to claim 6 wherein the attachment means comprises a body of resilient material into which an outer end of a needle can be embedded.

8. The apparatus according to claim 1 wherein the flexible cable has at least one bipolar electrode.

9. The apparatus according to claim 8 wherein the flexible cable further comprises two electrical conductors insulated with respect to each other, and where each conductor has an electrode.

10. The apparatus according to claim 9 wherein the flexible cable has a connector pin coupled to a proximal end of the flexible cable.

11. The apparatus according to claim 10 wherein the electrodes are spaced along the flexible cable.

12. The apparatus according to claim 11 wherein the electrodes are positioned as closely together as is possible while maintaining sufficient separation to prevent electrical shorting therebetween.

13. The apparatus according to claim 12 wherein there is a spacing of about 3 mm between the electrodes.

14. The apparatus according to claim 13 wherein one electrode is closer to a distal end of the flexible cable and is smaller than another larger electrode.

15. The apparatus according to claim 14 wherein the larger electrode comprises a contact surrounding both of the wires and is electrically connected to one of the two wires.

16. The apparatus according to claim 15 wherein the smaller electrode comprises a contact on or defined by a portion of the other of the two wires.

17. The apparatus according to claim 16 wherein the smaller electrode comprises an exposed section of the other wire.

18. The apparatus according to claim 17 wherein the exposed section of said other wire comprising a plurality of strips each of which is attached at a common end thereof to the remainder of the insulation, the plurality of strips being moveable between a collapsed condition in which the strips lie snugly against the exposed section of the wire and an extended condition in which the strips project outwardly of the wire to provide a barber formation, the strips being biased into the extended condition.

* * * * *